(12) United States Patent
Mostaghel et al.

(10) Patent No.: US 10,174,403 B2
(45) Date of Patent: Jan. 8, 2019

(54) METHODS AND APPARATUS FOR METAL RECOVERY FROM SLAG

(71) Applicant: HATCH LTD., Mississauga (CA)

(72) Inventors: Sina Mostaghel, Toronto (CA); Matthew H. Cramer, Milton (CA); Santiago Faucher, Oakville (CA); Lai Chi So, Mississauga (CA); Johannes Nell, Johannesburg (ZA)

(73) Assignee: Hatch, LTD, Mississauga, ON (CA)

( * ) Notice: Subject to any disclaimer, the term of this patent is extended or adjusted under 35 U.S.C. 154(b) by 0 days.

(21) Appl. No.: 15/537,708

(22) PCT Filed: Dec. 14, 2015

(86) PCT No.: PCT/CA2015/051320
§ 371 (c)(1),
(2) Date: Jun. 19, 2017

(87) PCT Pub. No.: WO2016/095031
PCT Pub. Date: Jun. 23, 2016

(65) Prior Publication Data
US 2017/0362680 A1    Dec. 21, 2017

Related U.S. Application Data

(60) Provisional application No. 62/094,370, filed on Dec. 19, 2014.

(51) Int. Cl.
| | | |
|---|---|---|
| C22B 7/00 | (2006.01) |
| C22B 7/04 | (2006.01) |
| B03C 1/02 | (2006.01) |
| B22F 9/08 | (2006.01) |
| C01B 13/16 | (2006.01) |
| C01B 13/34 | (2006.01) |
| C01G 55/00 | (2006.01) |
| C04B 5/00 | (2006.01) |
| G01N 33/20 | (2006.01) |

(52) U.S. Cl.
CPC ............... *C22B 7/04* (2013.01); *B03C 1/02* (2013.01); *B22F 9/082* (2013.01); *C01B 13/16* (2013.01); *C01B 13/34* (2013.01); *C01G 55/004* (2013.01); *C04B 5/00* (2013.01); *C22B 7/005* (2013.01); *G01N 33/20* (2013.01); *B03C 2201/20* (2013.01); *B22F 2009/0824* (2013.01); *C01P 2006/80* (2013.01); *Y02P 10/212* (2015.11)

(58) Field of Classification Search
CPC .. C22B 7/04; C22B 7/005; C04B 5/00; C01B 13/34; C01B 13/16; B22F 9/082; C01G 55/004; B03C 1/02
See application file for complete search history.

(56) References Cited

U.S. PATENT DOCUMENTS

| | | |
|---|---|---|
| 3,106,447 A | 10/1963 | Charvat |
| 3,300,300 A | 1/1967 | Blanks et al. |
| 3,868,440 A | 2/1975 | Lindblad et al. |
| 4,185,997 A | 1/1980 | Inoue et al. |
| 4,218,201 A | 8/1980 | Kozima et al. |
| 4,352,764 A | 10/1982 | Metz et al. |
| 4,359,434 A | 11/1982 | Tiberg |
| 4,671,752 A | 6/1987 | Nakahara et al. |
| 5,496,526 A | 3/1996 | Pojar et al. |
| 6,251,160 B1 | 6/2001 | Edlinger |

FOREIGN PATENT DOCUMENTS

| | | |
|---|---|---|
| CN | 101259991 A | 9/2008 |
| CN | 102453781 A | 5/2012 |
| CN | 102952908 A | 3/2013 |
| CN | 104141027 A | 11/2014 |
| EP | 1152064 A2 | 11/2001 |
| JP | 5487605 A | 7/1979 |
| JP | 2007-239034 A | 9/2007 |
| JP | 2013173994 A | 9/2013 |
| WO | 01/88206 A1 | 11/2001 |
| WO | 2012033454 A1 | 3/2012 |
| WO | 2015184533 A1 | 12/2015 |

OTHER PUBLICATIONS

Translation of CN 102453781 A. (Year: 2012).*
English Machine Translation of JPS 54-87605A dated Jul. 12, 1979.
English Machine Translation of JP 2013-173994A dated Sep. 5, 2013.
Canadian Intellectual Property Office, International Search Report with Written Opinion issued in PCT/CA2015/051320, dated Feb. 24, 2016, 17 pages, Canadian Intellectual Property Office, Gatineau, Quebec, Canada.

* cited by examiner

*Primary Examiner* — Steven J Bos
(74) *Attorney, Agent, or Firm* — Marshall & Melhorn, LLC (57) ABSTRACT

A method for recovering metal values from a molten slag composition includes atomizing the slag with an oxygen-containing gas in a gas atomization apparatus, to produce solid slag granules. Oxygen in the atomizing gas converts metals to magnetic metal compounds, thereby magnetizing the metal-containing slag granules. These metal-containing slag granules are then magnetically separated. Larger amounts of metals may be removed by passing the molten slag through a pre-settling pan with an adjustable base, and/or discontinuing atomization where the metal content of the slag exceeds a predetermined amount. Solid slag granules produced by atomization may be charged to a recovery unit for recovery of one or more metal by-products. An apparatus for recovering metal values from molten slag includes a gas atomization apparatus, a flow control device for controlling the flow of atomizing gas, a control system, and one or more sensors to detect metal values in the slag.

5 Claims, 5 Drawing Sheets

METHODS AND APPARATUS FOR METAL RECOVERY FROM SLAG

CROSS-REFERENCE TO RELATED APPLICATION

This application claims priority to and the benefit of U.S. Provisional Patent Application No. 62/094,370 filed Dec. 19, 2014, the contents of which are incorporated herein by reference.

FIELD

The present disclosure relates to methods and apparatus for recovery of metals from slag, and particularly to methods and apparatus wherein molten slag from a metallurgical furnace is subjected to gas atomization.

BACKGROUND

Slag is a by-product of metal production processes conducted in metallurgical furnaces. During metal production, slag is present in the metallurgical furnace in molten form. Molten slag is periodically or continuously tapped from the furnace for disposal and/or further processing. Inevitably the tapped slag stream will contain one or more metal values, including entrained particles or droplets of molten metal which have been produced in the furnace. Although measures may be taken to reduce the loss of metal values in the molten slag stream, such measures are only partly successful. As a result, the entrainment of metals represents a loss ranging from 0.1 to 5% (typically about 1-2%) of the metal produced in the furnace. Additionally, in some specific operations, inefficiency and/or poor operational control can result in discrete events which result in large volumes of metal being lost to the slag stream.

The slag stream may also contain one or more other metal values, which could be extracted in the downstream operations as by-products of the process. In some cases these metallic by-products may be of significant value.

Once it is tapped, the molten slag is typically allowed to cool and solidify in large masses. Recovery of metal values from the solidified slag is extremely difficult and costly due to the need for handling the large masses of solidified material, and crushing the material to a size which makes metal recovery possible through any physical or chemical process.

For example, one common separation method includes the steps of: 1) transporting and dumping the slag; 2) natural cooling and solidification or in some cases use of water spray to accelerate the cooling process; 3) crushing and grinding the solidified slag; and 4) magnetic separation. However, there are several problems associated with this method, including: the need for significant space for dumping and cooling of the slag; safety concerns due to transporting large volumes of slag to the dumping area; the risk of explosion from spraying water on the molten slag; and dust creation during the crushing/grinding process. Furthermore, the recovery of non-magnetic metals/alloys such as FeMn is even more complicated.

There remains a need for effective processes and apparatus for recovery of entrained metals and/or metal by-products from molten slag streams, which avoid the difficulties and costs associated with handling and crushing of solidified slag.

SUMMARY

In an embodiment, there is provided a method for separating a metal-rich fraction from a slag composition, the method comprising: (a) providing said slag composition in molten form, wherein the slag composition contains one or more metal values; (b) feeding the molten slag composition to an atomization chamber of a gas atomization apparatus; (c) feeding a stream of a gas into the atomization chamber through an atomization nozzle, wherein the gas contains oxygen; (d) atomizing the molten slag composition with the stream of gas in the atomization chamber to disperse and solidify the molten slag product to form solid slag granules, wherein the gas contains oxygen in a sufficient concentration to convert at least a portion of the one or more of the metal values to one or more magnetic metal compounds during the atomization of the molten slag composition, wherein the presence of said magnetic metal compounds in sufficient concentrations in a first fraction of the solid slag granules renders the granules of the first fraction sufficiently magnetic to permit them to be separated from the remainder of the solid slag granules by magnetic means; and (e) magnetically separating the first fraction from the remainder of the solid slag granules.

In one aspect, the one or more metal values are selected from one or more members of the group comprising: entrained non-magnetic metals or alloys, and chemically dissolved metals or alloys.

In another aspect, the magnetic metal compounds comprise one or more spinel structures having the general formula $AB_2O_4$, wherein A is a divalent cation and B is a trivalent cation.

In yet another aspect, the gas comprises air.

In yet another aspect, the method further comprises the step of controlling the partial pressure of oxygen in the gas so that the slag lies in the spinel primary crystallization phase field.

In yet another aspect, the method further comprises the step of tapping the molten slag composition from a metallurgical furnace and transporting the molten slag composition from the furnace to the gas atomization apparatus while maintaining the slag composition in its molten state.

In yet another aspect, the method further comprises the step of returning the first fraction of the solid slag granules to the metallurgical furnace for re-smelting.

In another embodiment, there is provided a method for recovering one or more metal values entrained in a molten slag composition, the method comprising: (a) providing said molten slag composition; (b) transporting said molten slag composition toward an atomization chamber of a gas atomization apparatus; (c) determining whether an amount of said one or more metal values entrained in the molten slag composition exceeds a predetermined amount; and (d) where it is determined that the amount of said one or more metal values entrained in the molten slag composition is less than the predetermined amount, the method further comprises the step of atomizing the molten slag composition with a stream of gas produced by one or more atomization nozzles located in the atomization chamber, to disperse and solidify the molten slag product to form solid slag granules; or (e) where it is determined that the amount of said one or more metal values entrained in the molten slag composition exceeds the predetermined amount, the method further comprises the step of permitting the molten slag composition to cool and solidify without being atomized by said stream of gas in the atomization chamber.

In one aspect, the step of determining an amount of said one or more metal values entrained in the molten slag composition is performed by visual inspection or by one or more sensors.

In another aspect, the one or more sensors are selected from the group comprising infrared, light, thermal sensors, and compositional sensors (which can be an X-ray Diffraction (XRD), an X-ray Fluorescence Spectrometer (XRF), Spectral, gas, magnetic).

In yet another aspect, the one or more sensors are located inside and/or upstream and/or downstream of the gas atomization apparatus.

In yet another aspect, the step of determining an amount of said one or more metal values entrained in the molten slag composition is performed on a continuous or intermittent basis.

In yet another aspect, the molten slag composition enters the gas atomization chamber and passes in front of said one or more gas atomization nozzles.

In yet another aspect, during step (d), the solid slag granules collect in a first area of the gas atomization chamber.

In yet another aspect, during step (e), the stream of gas from the one or more nozzles is discontinued.

In yet another aspect, during step (e), the stream of gas is discontinued by diverting the gas stream and/or discontinuing or reducing a flow of said gas to the one or more nozzles.

In yet another aspect, the diversion of the gas stream and/or the discontinuance of the flow of said gas is controlled by a control system which receives electronic signals from the one or more sensors.

In yet another aspect, during step (e), the slag composition is permitted to cool and solidify in a second area of the gas atomization chamber which is separate from the first area.

In yet another aspect, the method further comprises the step of transporting the cooled and solidified slag composition produced during step (e) to a metal recovery unit, and recovering said one or more metal values in the metal recovery unit.

In yet another aspect, the method further comprises the step of tapping the molten slag composition from a metallurgical furnace and transporting the molten slag composition to the gas atomization apparatus in a slag launder.

In yet another aspect, the method further comprises the step of passing the molten slag composition through a pre-settling pan as it flows toward the gas atomization apparatus.

In yet another aspect, the method further comprises adjusting a volume of the pre-settling pan by raising or lowering a base of the pre-settling pan.

In yet another aspect, the volume of the pre-settling pan is adjusted in relation to an amount of said one or more metal values entrained in the molten slag composition.

In yet another aspect, the volume of the pre-settling pan is enlarged in response to increasing levels of said one or more metal values in the molten slag composition, and the volume of the pre-settling pan is reduced in response to decreasing levels of said one or more metal values in the molten slag composition.

In another embodiment, there is provided an apparatus for recovering one or more metal values entrained in a molten slag composition, the apparatus comprising: (a) a gas atomization apparatus having an atomization chamber containing one or more atomization nozzles; (b) a flow control device for alternately supplying and discontinuing a supply of atomizing gas to said one or more atomization nozzles; (c) a control system which controls the operation of said flow control device; and (d) one or more sensors located at and/or upstream and/or downstream of the atomization chamber, wherein said one or more sensors are adapted to detect said one or more metal values in the molten slag composition, and to provide electronic signals to the control system indicating the presence or absence of said one or more metal values.

In one aspect, the flow control device comprises a valve for alternately supplying the flow of the atomizing gas to the one or more atomizing nozzles and discontinuing the flow of the atomizing gas to the one or more atomizing nozzles.

In another aspect, the apparatus further comprises an exhaust port for exhausting the atomizing gas which is diverted from the one or more atomization nozzles.

In yet another aspect, the apparatus further comprises a blower which supplies a flow of the atomizing gas to the one or more atomization nozzles, and wherein the flow control device is adapted to control the flow of the atomizing gas produced by the blower.

In yet another aspect, the flow control device comprises a diversion/switching unit.

In yet another aspect, the apparatus further comprises a pre-settling pan located upstream of the atomization chamber, wherein the pre-settling pan has an adjustable volume.

In yet another aspect, the pre-settling pan has a base comprising a sand layer and a movable plate located below the sand layer.

In yet another aspect, the pre-settling pan further comprises a mechanism for raising and lowering the movable plate.

In yet another aspect, the mechanism for raising and lowering the movable plate comprises a hydraulic ram.

In yet another aspect, the control system controls the operation of said pre-settling pan.

In another embodiment, there is provided a method for recovering one or more metals from a slag composition as by-products of the operation, the method comprising: (a) providing said slag composition containing said one or more metals, wherein the slag composition is in molten form; (b) feeding the molten slag composition to an atomization chamber of a gas atomization apparatus; (c) feeding a stream of a gas into the atomization chamber through an atomization nozzle; (d) atomizing the molten slag composition with the stream of gas in the atomization chamber to disperse and solidify the molten slag product to form solid slag granules; and (e) charging the solid slag granules to one or more recovery units to recover said one or more metals from the solid slag granules as by-products of the operation.

In one aspect, the method further comprises the step of pre-treating the solid slag granules in a preparation unit, wherein the pre-treating step is performed between steps (d) and (e).

In another aspect, the pre-treating step comprises a physical pre-treatment or a chemical pre-treatment.

In yet another aspect, the physical pre-treatment may comprise magnetic separation and/or size reduction.

In yet another aspect, the chemical pre-treatment may comprise treatment in a fluidization bed and/or roasting unit.

In yet another aspect, the metal recovery unit comprises a pyrometallurgical or hydrometallurgical processing unit, selected from a fuming furnace, a top blown rotary converter (TBRC or kaldo furnace), a rotary kiln, an electric furnace, or an acid leaching unit.

BRIEF DESCRIPTION OF THE DRAWINGS

The invention will now be described, by way of example only, with reference to the attached drawings, in which.

DETAILED DESCRIPTION

The following is a detailed description of metallurgical processes and facilities for recovery of metals from slag, wherein a stream of molten slag tapped from a metallurgical furnace is subjected to gas atomization in a gas atomization plant.

In particular, the invention relates to the practical application of dry slag atomization technology to the handling of slags containing metal/alloy values. The equipment and control/operating philosophies disclosed herein allow operators to benefit from the lower operating costs and environmental benefits of dry slag atomization while minimizing metal losses to the slag phase.

A first embodiment of a method and apparatus for recovery of metals from slag is now described below with reference to FIG. 1, which illustrates a metallurgical furnace 10 including a plurality of electrodes 12 for supplying heat to produce and maintain a layer of molten metal 14 and a layer of molten slag 16 within the furnace. The furnace 10 includes a slag tap hole 18 which communicates with the molten slag layer 16 and a molten metal tap hole 20 which communicates with the molten metal layer 14. Although furnace 10 is shown as having separate slag and metal tap holes 18, 20, it will be appreciated that many furnaces 10 have a single tap hole for tapping metal and slag. Therefore, throughout this application the term "tap hole" includes dedicated slag tap holes and tap holes for tapping metal and slag.

Molten slag is tapped periodically or continuously from the furnace 10 through the tap hole 18, and may be tapped into a movable slag vessel (such as a slag pot or ladle) or a slag launder or runner, in which it is transported to another area of the plant. During transport, the slag is maintained in a molten state. The transportation of the molten slag in a slag vessel or launder is represented by arrow 22 in FIG. 1.

Figure 1:
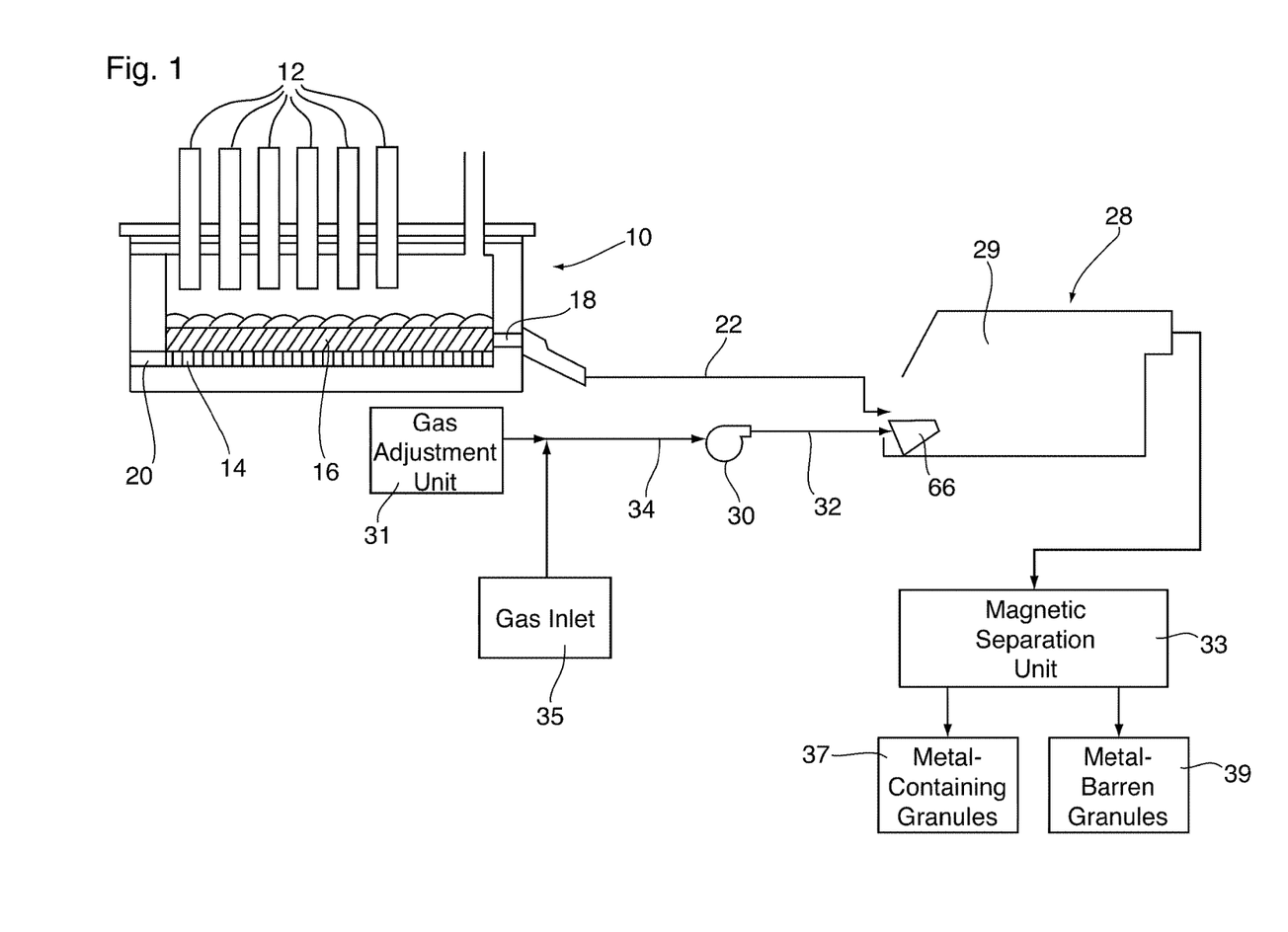
FIG. 1 illustrates a method and apparatus for magnetic separation of metal-containing granules from molten slag according to a first embodiment described herein.

Also shown in FIG. 1 is a gas atomization plant 28 having a gas atomization chamber 29 in which the molten slag is atomized to produce solid slag granules. The gas atomization plant 28 is located in close proximity to the metallurgical furnace 10, and receives the molten slag from furnace 10 via the movable slag vessel or launder 22.

Inside the chamber 29 of plant 28 the molten slag is atomized by one or more gas streams from one or more atomization nozzles 66, wherein the one or more nozzles 66 are supplied with atomization gas by an induced draft (ID) fan 30 (also sometimes referred to herein as "blower 30"), which in turn receives the atomization gas through a conduit 34 from a gas inlet 35. The supply of atomizing gas from the ID fan 30 to gas atomization plant 28 is represented by arrow 32 in FIG. 1. When the gas stream from nozzle 66 contacts a falling stream of molten slag in the atomization chamber 29 of gas atomization plant 28, the molten slag is simultaneously separated into droplets and cooled to a solid state, thereby forming solid slag granules which fall to the bottom of the chamber 29. The use of gas atomization can avoid, simplify or reduce the need for an expensive and dust-creating crushing and size-reduction of solidified slag, and prepares the material for a downstream metal recovery step.

According to the present embodiment, the gas flow for atomizing the molten slag contains oxygen, and may comprise ambient air. The oxygen in the atomizing gas converts non-magnetic entrained particles of metal and/or metal alloys in the slag to highly magnetic spinel structures having the general formula $AB_2O_4$ wherein A represents a divalent cation and B represents a trivalent cation. For example, the spinel jacobsite ($MnFe_2O_4$) may be produced from FeMn droplets present in the molten slag. Other potential spinels to be produced can be shown by this general chemical formula:

$$(Fe,Co,Mg,Mn,Ni,Zn)[Fe,Al,Cr]_2O_4$$

The magnetic properties of spinels permit them to be easily separated using a magnetic field in a magnetic separation unit 33 located downstream of the gas atomization plant 28, and the fine particle size of the atomized slag granules can eliminate the need to crush or grind the slag granules. In the magnetic separation unit 33 the atomized slag granules are magnetically separated into metal-containing granules 37 and metal-barren granules 39. The metal-containing granules 37 may be directly returned to the furnace for re-smelting or any other metal recovery operation/unit process.

During the atomization, the oxygen partial pressure of the atomizing gas is controlled so that the slag lies in the spinel primary crystallization phase field. Therefore, the first crystals to precipitate from the melt during the atomization will be spinels. Rapid solidification of the material does not allow these extremely fine crystals to grow, however, their mere formation is enough to produce magnetic properties. Very fine crystals can coexist with the glassy matrix in a manner that is not distinguishable by the commonly used characterization techniques as have been reported for zinc slags, medieval slags and laterite smelting slags. However, the production of fine particles by gas atomization, and potentially further crushing/grinding, allows separation of these fine spinel-rich domains from the bulk of the glassy material using magnetic separation.

The need for additional size-reduction is extremely dependent on slag composition and atomization parameters (e.g. air/slag ratio and thereby particle size distribution of the atomized slag). Spinel domains should be larger than a specific proportion of the total mass of the granules so that the magnetic field is able to separate spinel-rich particles from the rest of the atomized slag. If the size of granules is too large (i.e. the relative concentration of spinel in that granule is low), the magnetic field cannot separate it and further size reduction (grinding) is required. The need for further size reduction must therefore be determined on a case-by-case basis.

As mentioned above, the oxygen concentration of the atomization gas may be adjusted to optimize the conversion of the non-magnetic entrained metal/alloy particles in the slag to highly magnetic spinel structures. The required oxygen concentration will depend largely on the spinel species which are to be formed, which of course depends on the composition of the slag. While ambient air may be suitable for spinel formation under some conditions, in some cases it may be necessary to enrich the oxygen content of the atomization gas by mixing oxygen or an oxygen-enriched gas stream with the atomization gas. In other cases it may be necessary to dilute the oxygen content of the atomization gas, for example by mixing an oxygen-free or oxygen- depleted gas stream with the atomization gas. For example, where the atomization gas is ambient air, it may be enriched by the addition of oxygen or diluted by the addition of nitrogen. FIG. 1 shows a gas adjustment unit 31 through which additional gas may be added to the gas stream in conduit 34, for the purpose of enriching or diluting the oxygen content of the atomization gas.

In addition to achieving separation of entrained metals in the slag, for example in the form of droplets, the present embodiment also achieves separation of chemically dissolved metal values in the slag, such as iron in basic oxygen furnace (BOF) slags. By adjusting the oxygen content of the atomization gas, the metal (in this case iron) will be converted to spinel-type oxide (in this case magnetite). By applying a magnetic field, the metal-rich granules (spinels) can be separated and recycled back to the furnace, increasing the efficiency of the operation.

As another example, the present embodiment may also be used for recovery of nickel from the slag produced by ferronickel smelters. Typically, the entrainment of FeNi droplets in the slag phase is limited. It is generally estimated that chemically dissolved and mechanically entrained Ni would be ~0.2 wt-% in the slag phase. However, the rate of slag generation in ferronickel smelting is very large, with a typical ferronickel smelter producing 800,000 tonne/year slag. Therefore, total metal loss of ~1,600 tonnes of Ni/year is expected from a typical ferronickel smelter. According to the present embodiment, at least a portion of this metal value may be recovered with a cost-effective method of atomization followed by magnetic separation.

The present embodiment may also be used for recovery of iron and/or copper from the slag produced by copper smelters. For most copper smelters, slag is rich in iron. Although several attempts have been made, no commercially viable method has been established for iron recovery from the copper smelting slag. According to the present embodiment, gas atomization with a controlled concentration of oxygen can oxidize the slag, forming spinel type oxides (magnetite, $FeFe_2O_4$) which can be separated by magnetic separation (at relatively low costs) and then charged to ironmaking/steelmaking furnaces.

Copper smelters may also suffer from high copper losses to their slag phase, particularly those which do not have a settling furnace. The copper rich slag is conventionally recycled to another type of process, such as a flotation or electric smelting furnace. However, these processes are costly and require a significant amount of material handling. In contrast, gas atomization of the copper rich slag according to the present embodiment also produces one or more copper-containing spinel type oxides (copper aluminate $CuAl_2O_4$, cuprospinel $CuFe_2O_4$, etc.), all of which are magnetic and can be separated by magnetic separation. These metal-rich magnetically separated materials can then be charged to a smelting furnaces or a convertor. As soon as copper oxide (in any form, spinel or cuprous oxide, $Cu_2O$) is charged into a matte bath, it re-establishes a new equilibrium with sulphides in the system and can be reduced to metallic copper or copper sulphides and hence can be recovered together with rest of the matte phase. The following reactions are expected to occur:

$Cu_2O+FeS \rightarrow Cu_2S+FeO$ $Cu_2S+2Cu_2O \rightarrow 6Cu^0+SO_2$

Figure 2:
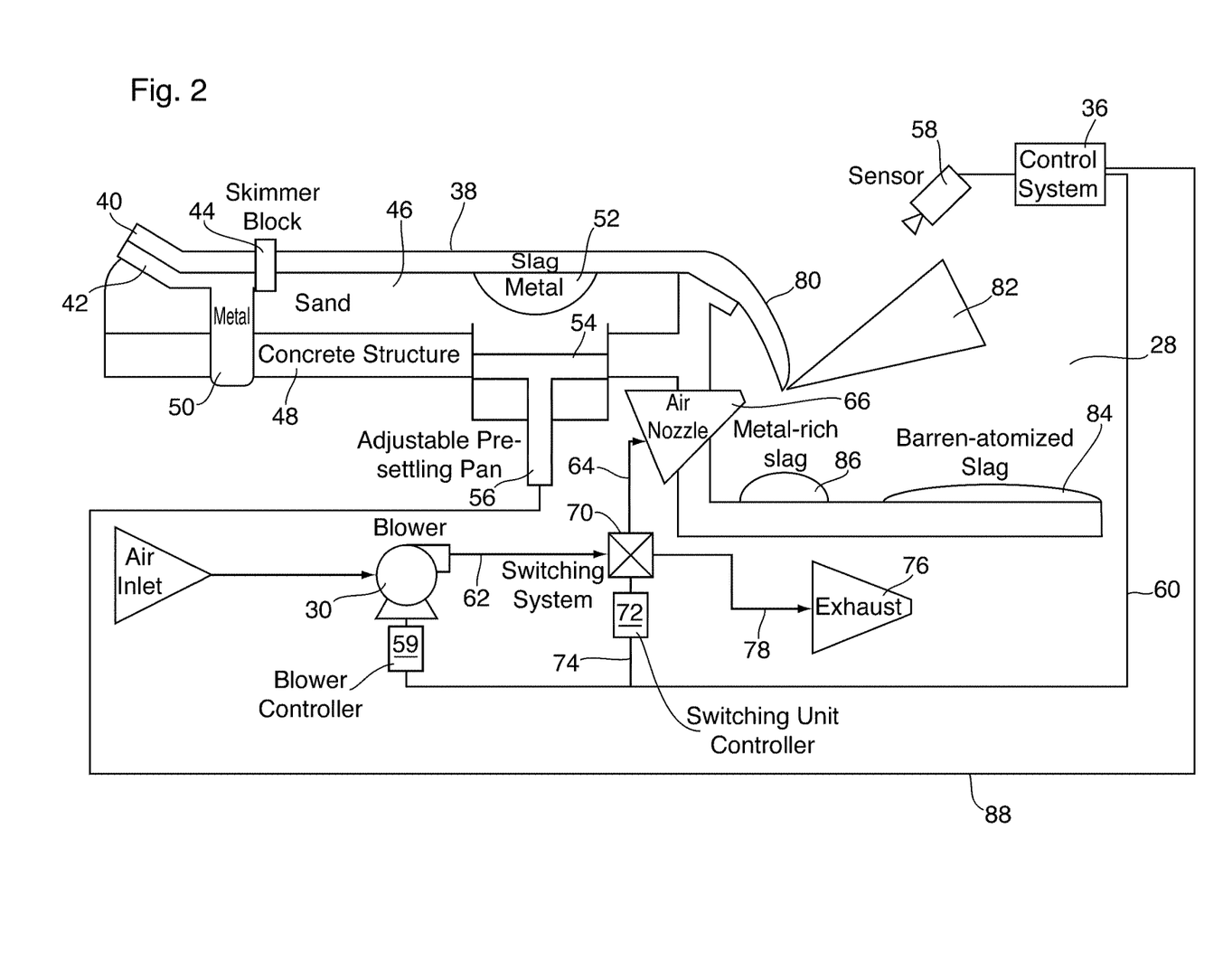
FIG. 2 illustrates a method and apparatus for production of metal-rich and metal-barren slag fractions according to a second embodiment described herein.

A second embodiment of a method and apparatus for recovery of metals from slag is now described below with reference to FIG. 2. The second embodiment relates specifically to preventing the loss of entrained metal/alloy droplets from a metal-rich slag stream. FIG. 2 includes a number of components which are similar or identical to the components illustrated in FIG. 1, and these like components are identified by like reference numerals.

In a number of smelting operations, metal losses are of an intermittent and discrete nature. For example, poor post tap hole operational control such as tap hole plugging failures, skimmer block failures or launder leaks are discrete events that result in large volumes of metal being lost to the slag stream. If uncontrolled, these discrete events can "contaminate" the entire tap with a mixture of metal and slag, which requires the entire slag tap to be treated for metal recovery.

For example, in conventional operations, once a large metal stream is introduced to the slag cooling pit the entire pit is considered "contaminated" and what was barren slag is now metal-enriched and must be treated. Due to the slow air cooling of the material, the only effective means to reclaim the metal is to crush and jig the entire contents of the pit. Jigging is a water based process which exploits density differences to separate a concentrated metal stream from a barren slag stream. Jigging adds additional costs and results in both environmental and safety concerns.

In processes where slag pots are used to transport slag, metal present in the slag will sink to the bottom of the pot. Since these pot comprise unlined cast steel, the additional heat transfer from the molten metal immediately elevates the risk profile of the operation. Metal-containing slag pots must be removed from the process and allowed to cool over several days, resulting in a reduction in available pots and complications in removing the solidified material from the pot. After removal, the entire pot contents must be crushed and processed in a metal recovery plant.

It is estimated that 80% of the metal lost during these discrete events is contained in only 15-20% of the slag. The balance of the slag is for all intents and purposes metal barren, but must be processed to recover the lost metal.

The present embodiment permits these discrete events to be isolated so as to minimize the volume of slag required to be processed to recover the metal. The apparatus of the present embodiment includes one or more of the following components to minimize the metal loss:

a pre-settling pan 52 which may be fixed or adjustable;

a dry slag gas atomization plant 28 similar to that described above with reference to the first embodiment shown in FIG. 1; and a control system 36 allowing automatic diversion of the metal-rich stream.

The above components are described in more detail below.

In the second embodiment, molten slag 40 is tapped periodically or continuously from the tap hole of a metallurgical furnace (not shown), exactly as described in the first embodiment. The molten slag 40 may be transferred from the furnace toward the gas atomization plant 28 in a number of ways, such as a slag vessel or launder. In the illustrated embodiment, the molten slag 40 flows along a slag launder 38. The slag launder 38 is shown in this example as comprising a layer of sand 46 supported on a concrete structure 48.

The molten slag 40 is shown as including metal 42. The metal 42 has greater density and therefore settles to the bottom as it flows toward the gas atomization plant 28. The metal 42 and slag 40 are shown in FIG. 2 as comprising separate layers in order to illustrate that metal is of greater density and will tend to settle out of the slag. However, it will be appreciated that at least a portion of the metal 42 will be entrained in the slag 40 in the form of droplets.

A partial separation of metal 42 and slag 40 may be achieved by a carbon skimmer block 44, which diverts the main portion of the metal 42 into a depression 50 in the sand layer, while permitting the remainder of the molten material (comprising slag and any remaining metal) to flow toward the gas atomization plant 28. A similar separation can be achieved by collecting the molten slag 40 in a ladle (not shown), and allowing the metal 42 to settle to the bottom of the vessel while the slag overflows the vessel and flows toward the gas atomization plant 28.

The carbon skimmer block 44 or ladle each have a limited ability to recover metal from the molten slag 40. For example, poor post tap hole operations (namely runner failure, skimmer block collapse, tap gun hydraulic failure, late closing tap hole) and turbulent flow will result in entrained metal droplets reporting to the slag stream and not settling sufficiently to be retained in the metal ladle or casting area. These values can represent between 2% and 5% of the slag mass as clean alloy. In conventional operations, this metal is recovered by cooling and solidifying the vast majority of the slag in a pit or slagpot/ladle before being crushed and fed to a jigging process in a metal recovery plant. This costly and inefficient step is avoided in the present embodiment, as follows.

Firstly, in addition to the carbon skimmer block 44 or slag vessel, the apparatus of FIG. 2 further comprises a pre-settling pan 52 over which the slag 40 flows on its way to the gas atomization plant 28. The pre-settling pan 52 comprises a depression in the sand layer 46 into which the entrained droplets of metal 42 settle and separate from the molten slag 40. The capacity of the pre-settling pan 52 can be adjusted to treat slag with higher or lower metal contents, thereby increasing the recovery capability. To adjust the volume of pan 52 in relation to the content of metal 42 in the slag 40, the apparatus according to the second embodiment comprises a movable plate 54 located beneath or within the sand layer 46, beneath the pan 52, and means for raising and lowering the plate 54 so as to raise or lower the base of the pan 52. In the illustrated embodiment, a hydraulic ram 56 may be provided below plate 54 for this purpose.

The adjustable pre-settling pan 52 allows the operator to capture entrained metal prior to atomization, when the metal losses are continuous, and make up a small portion of the slag stream. The adjustable nature allows the operator to limit the amount of slag entering the pan 52 and to ensure that even when a crust forms in the pan 52 due to cooling, additional volume can be made available for metal capture. Removing the final ingot from pan 52 is simplified by the design and utilises existing equipment.

Secondly, the present embodiment provides means for substantially avoiding atomization of slag 40 containing high amounts of metal 42. After flowing through and/or over the pre-settling pan 52, the molten slag 40 flows through launder 38 toward the gas atomization plant 28. As it flows through launder 38, the composition of the slag 40 is intermittently or continuously monitored to detect high concentrations of metal 42. What is considered to be a high concentration will depend on a variety of factors, and is of course process-specific.

In the present embodiment, the composition of the slag 40 is intermittently or continuously monitored by visual observation of the operator and/or one or more sensors 58, which may include infrared sensors, light sensors, thermal sensors, and/or compositional sensors. Examples of compositional sensors include X-ray Diffraction (XRD) sensors, X-ray Fluorescence Spectrometers (XRF), Spectral sensors, gas sensors and magnetic sensors. For example, this monitoring by sensor(s) 58 may detect the relatively higher energy release from the material as metal concentration increases (as a result of exothermic metal oxidation), and/or the changed emission spectrum of the blast when metal-rich slag is atomized in the gas atomization plant 28. This allows fast and accurate detection of any metal-rich portions of slag 40 that are tapped from the furnace 10. The sensor(s) 58 may be located upstream of, downstream of, and/or inside the gas atomization plant 28.

The sensor(s) 58 generate and send electronic signals to the control system 36, wherein the signals relate to the composition of the slag 40. Once it is determined that the slag 40 flowing toward the gas atomization plant 28 contains excessive amounts of metal 42, the control system 36 actuates one or more mechanisms to prevent atomization of the slag until the signals from sensor 58 indicate that the concentration of metal 42 in the slag 40 has again reached an acceptable concentration.

It will be appreciated that the operation of the pre-settling pan 52 described above may also be controlled by the control system 36. Therefore, the control system 36 may adjust the volume of pre-settling pan 52 by actuating hydraulic ram 56 to raise or lower the plate 54 in response to signals from the same or different sensor(s) 58 which are used to monitor the metal content of the molten slag 40. Therefore, as shown in FIG. 2, the control system 36 may be connected to the hydraulic ram 56, and this connection is indicated by line 88 in FIG. 2. Alternatively, or in addition to control by control system 36, the operation of the pre-settling pan 52 may be controlled and/or actuated by a human operator.

Two possible arrangements for controlling atomization of the slag 40 with control system 36 are illustrated in FIG. 2, and are now discussed below. It will be appreciated that these two arrangements can be used together or individually for control of slag atomization. Alternatively, or in addition to control by control system 36, the atomization of slag 40 may be controlled and/or actuated by a human operator.

According to the first arrangement, the control of slag atomization is accomplished by directly controlling the output of blower 30 so that the blower 30 is turned off or running at reduced speed during periods when the metal content of the slag 40 is unacceptably high, to thereby prevent the atomization of slag 40, and so that the blower 30 is operating to atomize the slag 40 during periods where its metal content is at an acceptable level. According to this arrangement, the control system 36 may be directly connected to the blower 30 or to a blower controller 59 for controlling the operation of the blower 30, and this direct connection is indicated by line 60 of FIG. 2. The control system 36 causes the blower 30 to be turned off or run at reduced speed during periods when the metal content of the slag 40 is unacceptably high, and until the sensors 58 and/or visual observation indicate that the concentration of metal 42 in the slag 40 has again reached an acceptable concentration, at which point the control system 36 will cause the blower 30 to return to normal operation and resume the atomization of the slag 40.

According to the second arrangement, the control of slag atomization is controlled by controlling the output of the blower 30 so that the blower output flows to an atomization nozzle 66 to atomize the slag 40 during periods where its metal content is at an acceptable level, and so that the blower output is completely or partially diverted away from atomization nozzle 66 to prevent atomization of slag 40 during periods when the metal content of the slag 40 is at an unacceptably high level.

Therefore, as shown in FIG. 2, the control system 36 may be connected to a diversion/switching unit 70, either directly or through a switching unit controller 72, and this connection is indicated by line 74 in FIG. 2. For convenience, FIG. 2 shows lines 60 and 74 as being combined along portions of their length. The diversion/switching unit 70 may comprise a three-way valve, which has a first port (also referred to herein as a "gas inlet port") communicating with the blower 30 to receive the blower output through a conduit 62, a second port communicating with the atomization nozzle 66 through a conduit 64 to direct the blower output to the nozzle 66, and a third port (also referred to herein as an "exhaust port") to divert the blower output away from nozzle 66, for example to an exhaust opening 76 through a conduit 78.

According to the second arrangement, the control system 36 controls the operation of the switching unit 70 and/or the switching unit controller 72 such that the switching unit 70 directs the blower output to the atomization nozzle 66 to atomize the slag 40 during periods where its metal content is at an acceptable level, and to direct the blower output away from atomization nozzle 66, for example to exhaust opening 76, so as to prevent atomization of slag 40 during periods when the metal content of the slag 40 is at an unacceptably high level.

As shown in FIG. 2, a stream of molten slag 40 falls into the atomization chamber from the end of slag launder 38. The falling stream of slag 40 is shown in FIG. 2 by reference numeral 80. During periods where the metal content of the slag 40 is determined to be at an acceptable level, a gas stream produced by the blower 30 is directed at the falling stream 80 of molten slag 40 by atomization nozzle 66. The contact of the falling stream 80 of molten slag 40 with gas from nozzle 66 causes the slag 40 to be separated into a plume of fine droplets which partially cool and solidify to form solid slag granules as they pass through the atomization chamber, wherein the plume of slag droplets is identified by reference numeral 82 in FIG. 2. Furthermore, the gas stream from nozzle 66 carries the slag granules away from the nozzle 66, and they are collected in a heap 84 on the floor of the atomization chamber some distance from the nozzle 66.

During periods where the metal content of the slag 40 is determined to be at an unacceptably high level, the atomization of the falling stream 80 of slag 40 is discontinued by stopping or reducing the flow of gas from the atomizing nozzle 66 by one of the arrangements described above. Therefore, under these conditions, the slag 40 is not atomized and simply falls to the floor of the atomization chamber in front of nozzle 66, and is allowed to cool and solidify into a mass 86.

As can be seen, the present method and apparatus provides a simple and effective means for separating the slag into metal-rich and metal-barren components. The relatively high volume metal-barren slag stream, which has been gas atomized, can be directly sold or stockpiled by the operator. This reduces overall post tap hole slag handling costs. On the other hand, the lower volume metal-rich slag stream is reclaimed and sent to the metal recovery plant. The separation of the slag into two product streams thereby significantly reduces the amounts of slag which need to be subjected to metal recovery. The separate treatment of the metal-rich slag lowers the cost of metal-reclaiming and unlocks the capacity within the existing metal recovery plant for the treatment of historical material which may be stockpiled and awaiting treatment. This allows the operator to both decrease slag treatment costs and increase saleable production of metal from that same equipment (due to the typically higher metal content of historical slag).

For example, by using the above described method and apparatus, about 80% of the slag may bypass the metal recovery plant. For a large ferrochrome facility producing approximately 400,000 tonnes of metal per year (tpa) this can equate to an additional 12,000 tpa or a 3% volume increase in metal production.

Also, in embodiments in which the control system 36 controls the operation of both the pre-settling pan 52 and the atomization plant 28, these two pieces of equipment can be operated in a co-ordinated manner to maximize the amount of metal 42 which is recovered from the slag 40. In this regard, the control system 36 may operate the pre-settling pan 52 to remove as much metal as possible from the molten slag 40. At least one sensor 58 may detect the metal content of the molten slag 40 downstream of the pre-settling pan 52, and the information provided to control system 36 by this sensor 58 may be used, at least in part, to control the operation of the gas atomization plant 28.

Although the second embodiment has been described in connection with specific metallurgical processes, it will be appreciated that the second embodiment is applicable to any molten materials atomization process where entrained particles in the molten material stream have financial benefits if removed prior to atomization, including such processes where the entrained particles are present in discrete periods during the atomization. Although ferrochrome production facilities have been specifically discussed above, it will be appreciated that the second embodiment is applicable to ferroalloy producers in general, e.g. those producing FeCr, FeNi, FeMn, etc. The second embodiment is also beneficial to steel producers to recover the iron content of the slag.

A method and apparatus for recovery of metals from slag according to a third embodiment is now described below. The third embodiment focuses on the treatment of slag to recover metallic by-products. This method comprises the following steps:

(a) providing said slag composition containing said one or more metal by-products, wherein the slag composition is in molten form;

(b) feeding the molten slag composition to an atomization chamber of a gas atomization apparatus;

(c) feeding a stream of a gas into the atomization chamber through an atomization nozzle;

(d) atomizing the molten slag composition with the stream of gas in the atomization chamber to disperse and solidify the molten slag product to form solid slag granules; and (e) charging the solid slag granules to one or more recovery units to recover said one or more metal by-products from the solid slag granules.

The method of the third embodiment may further include the step of pre-treating the solid slag granules in a preparation unit, wherein the pre-treating step is performed between steps (d) and (e). This pre-treating step may comprise one or more physical and/or chemical pre-treatment steps, and is at least partly dependent on the metal(s) being recovered. Specific examples of physical pre-treatments include magnetic separation and/or size reduction. Specific examples of chemical pre-treatments include treatment in a fluidization bed and/or roasting. However, it will be appreciated that this list of pre-treatments is not exhaustive, and may comprise one or more other pretreatment steps.

Similarly, the type of recovery unit used in step (e) is highly variable, and is at least partly dependent on the metal(s) being recovered. For example, the metal recovery unit may comprise a pyrometallurgical or hydrometallurgical processing unit, which may be selected from a fuming furnace, a top blown rotary converter (TBRC or kaldo furnace), a rotary kiln, an electric furnace, or an acid leaching unit.

After extraction of the metal of interest in a non-ferrous metal production plant, slag usually contains significant amounts of other valuable metallic elements including iron, zinc, cobalt etc. that should be recovered in subsequent processes in order to increase the overall economics of the operation. According to the present embodiment, gas atomization of slag is used to produce a material that can be directly treated in a subsequent process, thereby minimizing the preparation step that is typically required. This embodiment is illustrated by the following examples.

Lead (and in some cases copper) production slags may contain appreciable quantities of zinc, tin, germanium or cadmium. Therefore, further treatment of this slag in a fuming unit (being a conventional fuming furnace, a Waelz kiln, top blown submerged lance furnace or other fuming units) is a typical practice for metal recovery. Solidified and cooled slag needs to be crushed (and in some cases pelletized) before it can be charged to the fuming unit. However, by gas atomization of the slag, this pre-treatment step can be eliminated. Granules/pellets that are produced using the atomization process can be directly charged to a fuming unit.

For recovery of other by-product metal values e.g. iron and cobalt from a copper smelting slag, the solidified slag can be crushed, ground, and treated hydrometallurgically (e.g. acid leaching) to yield the remaining metals. Slag atomization can reduce the need for the expensive comminution process and allows the atomized/solidified slag to be treated in a hydrometallurgical operation, with no or limited amount of size reduction.

The treatment of molten slag by gas atomization according to the present embodiment provides additional advantages in the recovery of metallic by-products in that gas atomization may increase the reactivity of certain slags, which facilitates and/or accelerates the recovery of the metallic by-products in a leaching process. These advantages are further described below.

Firstly, it is to be noted that the rapid quenching of molten slag during gas atomization produces a glassy, amorphous material. Thermodynamically, such glassy materials have a higher internal energy and therefore glassy materials dissolve and react more readily in aqueous solutions than crystalline materials.

Secondly, rapid quenching of the molten slag by gas atomization can result in the formation of metastable phases, which are prone to react with an aqueous solution to reach stability. This will result in a more and faster leaching of gas atomized slags.

Therefore, it can be seen that the third embodiment facilitates process integration in non-ferrous metal production plants, in that the by-product (e.g. slag) of an operation to produce one metal becomes the feed material for another process producing another metal. This integration maximizes productivity from treatment of any given ore, thereby improving the sustainability and competitiveness of the smelter. Furthermore, the third embodiment may avoid the need for specific feed preparation of the slag, whether by drying, crushing, grinding, briquetting/pelletization, etc., which requires additional investment/operating and maintenance costs. The handling of gas atomized slag is more cost effective, robust and reliable, and may eliminate the need for expensive and dust-creating comminution operations.

In accordance with another embodiment, the recovery of metal from slag is enhanced by taking advantage of some slag's tendency to form slag wool during atomization. As discussed in International Application No. PCT/CA2015/050210, which is incorporated herein by reference in its entirety, slag wool is a by-product of the dry granulation of some types of slag. In the present embodiment, the wool fraction of the slag is separated to facilitate metal recovery. It is even possible to intentionally convert a proportion of slag to slag wool during gas atomization in order to enhance the recovery of metal from the slag.

Slag wool consists of low density fibers of slag produced by dry granulation of slag having poor droplet-forming properties, and/or high viscosity. Slag wool is of lower density than slag granules, is comprised primarily of silica, and typically has a low metal content. Therefore, where gas atomization produces an amount of slag granules and an amount of slag wool, the slag granules will tend to have a relatively high metal content, and the slag wool will tend to have a relatively low metal content. Therefore, the separation of the slag wool from the slag granules achieves at least a partial separation of a metal-rich fraction (slag granules) from a metal-barren fraction (slag wool) and, with the assistance of the above-described methods for recovering metal values from the slag granules, provides a more complete separation of the metal values from the slag.

Figure 3:
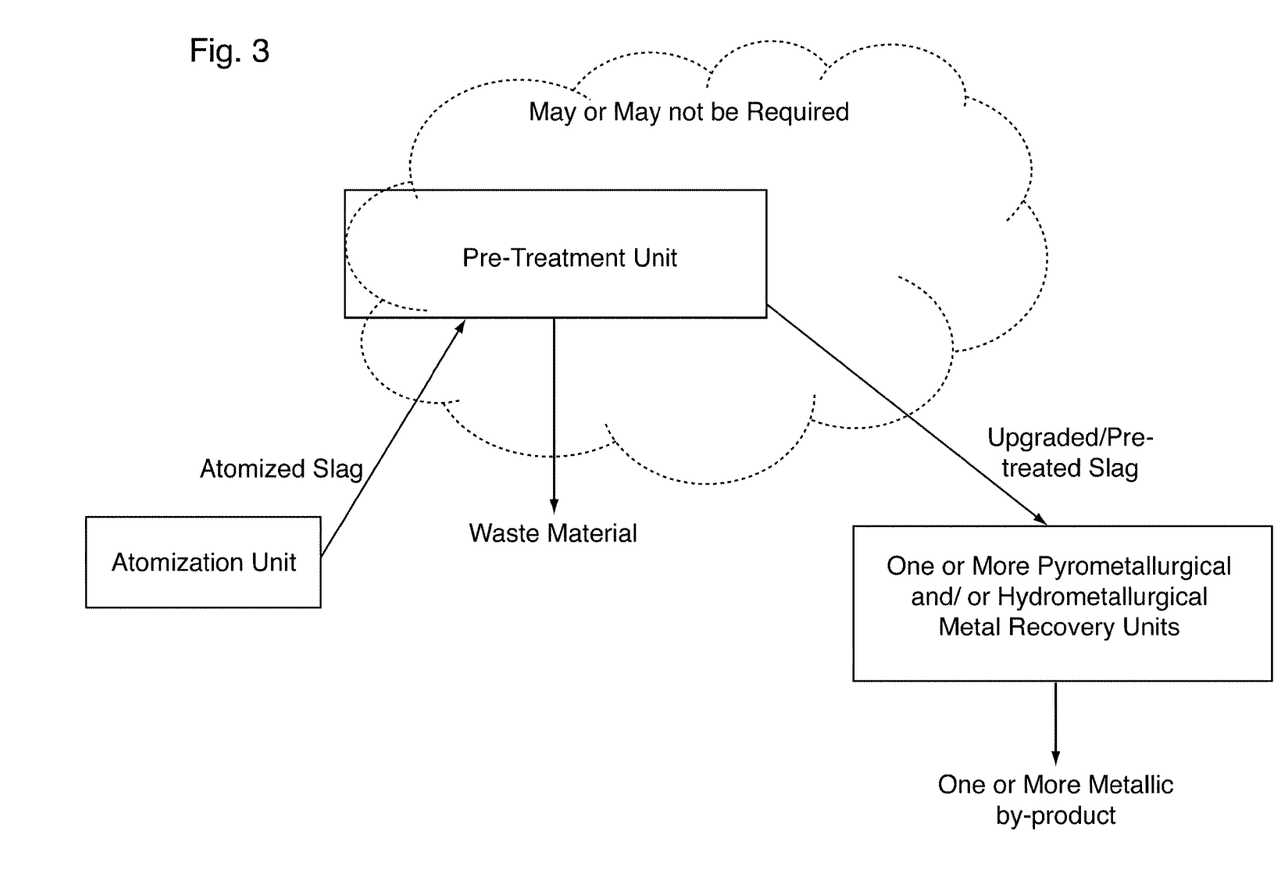
FIG. 3 illustrates a method and apparatus for recovery of metallic by-products from slag according to a third embodiment described herein.

In accordance with the present embodiment, molten slag is tapped from a furnace into a movable slag vessel or a slag launder or runner, in which it is transported to a gas atomization apparatus as described above with reference to any of FIGS. 1-3. During transport, the slag is maintained in a molten state. The gas atomization plant in the present embodiment is the same as described above with reference to any of FIGS. 1-3, having a chamber in which the molten slag is atomized by one or more gas streams from one or more atomization nozzles supplied with gas by an ID fan. Alternatively, the method according to the present embodiment can be adapted to the treatment of historical slags, wherein the historical slag is reduced in size and melted before being transported to a gas atomization apparatus in molten form.

Parameters of the atomization can be adjusted to control (increase or decrease) the amount of wool formation (to some extent). In the present embodiment, the gas atomization parameters are adjusted such that a proportion of the slag will be converted to slag wool, and a proportion of the slag will be converted to slag granules. The proportion of slag wool produced, as well as the parameters requiring adjustment, will depend to a large extent on the composition and viscosity of the slag, and on the amount of metal contained therein. In accordance with the present embodiment, the amount of slag wool production can be increased by one or more of the following methods: by adjusting the slag/gas ratio during atomization; by adjusting the temperature of the atomizing gas; by adjustment of the atomizing gas (eg. air) velocity; and by changing the chemical composition of the slag.

Once the slag is atomized, the chamber of the gas atomization plant will contain an amount of solid slag granules and an amount of slag wool. The slag granules can be separated from the wool on the basis of their higher density.

Once the slag granules are separated from the slag wool, they may be processed in accordance with the embodiments described above so as to recover metal from the granules. For example, the solid slag granules can be separated into one or more metal-rich fractions and one or more metal-barren fractions by magnetic separation, as discussed above.

Alternatively, the metal values can be recovered from the solid slag granules by one or more hydrometallurgical processes, as described above in connection with the third embodiment.

Figure 4:
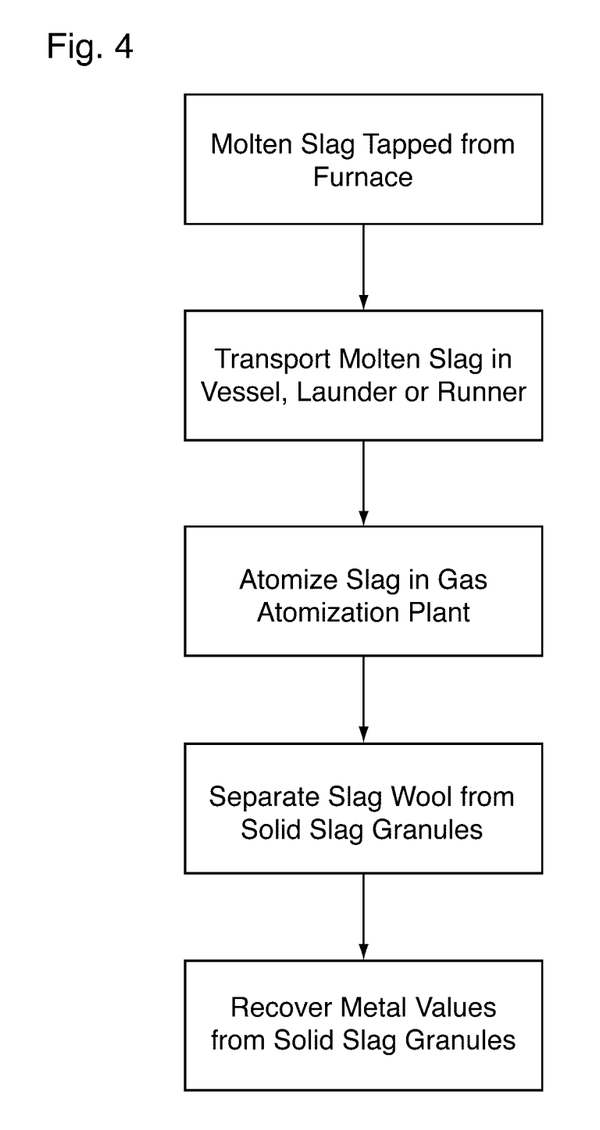
FIG. 4 is a process flow diagram for an embodiment in which an amount of slag wool is produced and then separated in order to enhance the separation of metals.

FIG. 4 is a process flow sheet outlining the above-described steps of the present embodiment.

In accordance with yet another embodiment, a process is described below for recovering platinum group metals entrained in molten slag produced during smelting of ores containing these metals. The platinum group metals comprise ruthenium (Ru), rhodium (Rh), palladium (Pd), osmium (Os), indium (In) and platinum (Pt).

Presently, the separation of platinum group metals from slag is achieved by maintaining the slag in molten form in a separate furnace, and allowing the entrained platinum group metals to separate from the slag by gravity (settling). This conventional process is not only time-consuming, due to the time required for the metal to separate from the slag, but large amounts of energy are required to keep the slag in molten form. Also, a dedicated furnace is required for the separation. In the present embodiment, the molten slag is tapped from a furnace into a movable slag vessel or a slag launder or runner, in which it is transported to a gas atomization apparatus as described above with reference to any of FIGS. 1-3. During transport, the slag is maintained in a molten state. The gas atomization plant in the present embodiment is the same as described above with reference to any of FIGS. 1-3, having a chamber in which the molten slag is atomized by one or more gas streams from one or more atomization nozzles supplied with gas by an ID fan. Alternatively, the method according to the present embodiment can be adapted to the treatment of historical slags, wherein the historical slag is reduced in size and melted before being transported to a gas atomization apparatus in molten form.

Figure 5:
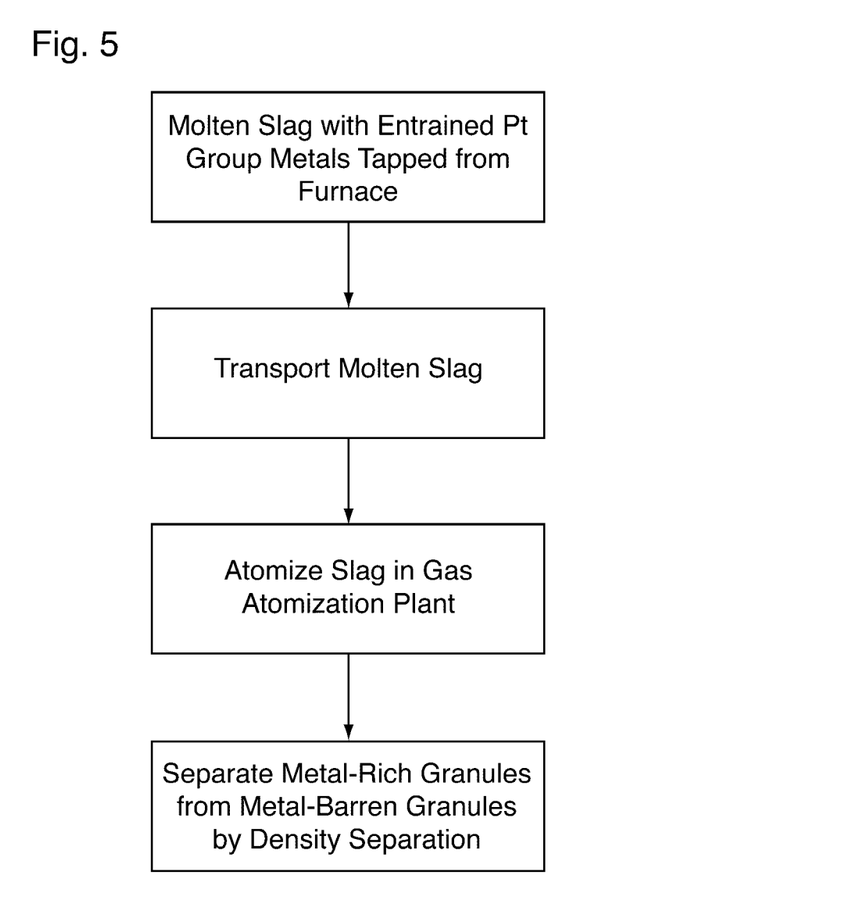
FIG. 5 is a process flow diagram for an embodiment in which platinum group metals are recovered from slag.

The atomization parameters are set such that the solid slag granules produced by the atomization will have a small particle size. The inventors have found that a phase separation between the metal phase and the slag phase will take place during atomization, such that the atomization will produce one or more fractions of slag granules which are rich in platinum group metals, and one or more fractions of slag granules which are barren in platinum group metals. After atomization, a simple density separation can be used for separating the metal rich and metal barren fractions from one another, or a magnetic separation may be used in some cases. FIG. 5 is a process flow sheet outlining the above-described steps of the present embodiment.

Although the invention has been described with reference to certain specific embodiments, it is not limited thereto. Rather, the invention includes all embodiments which may fall within the scope of the following claims.

What is claimed is:

1. A method for separating a metal-rich fraction from a slag composition, the method comprising:

(a) providing said slag composition in molten form, wherein the slag composition contains one or more metal values;

(b) feeding the molten slag composition to an atomization chamber of a gas atomization apparatus;

(c) feeding a stream of a gas into the atomization chamber through an atomization nozzle, wherein the gas contains oxygen;

(d) atomizing the molten slag composition with the stream of gas in the atomization chamber to disperse and solidify the molten slag composition to form solid slag granules, wherein the gas contains oxygen in a sufficient concentration to convert at least a portion of the one or more metal values to one or more magnetic compounds during the atomizing of the molten slag composition;

wherein the magnetic compounds comprise one or more spinel structures having the general formula $AB_2O_4$, wherein A is a divalent cation and B is a trivalent cation;

wherein the presence of said magnetic compounds in sufficient concentrations in a first fraction of the solid slag granules renders the granules of the first fraction sufficiently magnetic to permit them to be separated from the remainder of the solid slag granules by magnetic means;

(e) controlling the partial pressure of oxygen in the gas so that the molten slag composition has a composition which lies in thea spinel primary crystallization phase field; and (f) magnetically separating the first fraction from thea remainder of the solid slag granules.

2. The method of claim 1, wherein the one or more metal values are selected from one or more members of the group consisting of:

entrained non-magnetic metals or alloys, and chemically dissolved metals or alloys.

3. The method of claim 1, wherein the gas comprises air.

4. The method of claim 1, further comprising the step of tapping the molten slag composition from a metallurgical furnace and transporting the molten slag composition from the furnace to the gas atomization apparatus while maintaining the slag composition in its molten state.

5. The method of claim 4, further comprising the step of returning the first fraction of the solid slag granules to the metallurgical furnace for re-smelting.

* * * * *

UNITED STATES PATENT AND TRADEMARK OFFICE
CERTIFICATE OF CORRECTION

PATENT NO. : 10,174,403 B2
APPLICATION NO. : 15/537708
DATED : January 8, 2019
INVENTOR(S) : Lai Chi So et al.

Page 1 of 1

It is certified that error appears in the above-identified patent and that said Letters Patent is hereby corrected as shown below:

On the Title Page

Item (12), "Mostaghel, et al." should read -- So, et al. --

Item (72), The order of the Inventors names should appear as follows:
Lai Chi So
Matthew H. Cramer
Johannes Nell
Santiago Faucher
Sina Mostaghel In the Claims Claim 1,
Column 16, Line 36 delete word "thea" and insert -- a -- in its place
Column 16, Line 38 delete word "thea" and insert -- a -- in its place Signed and Sealed this
Eighth Day of October, 2019

Andrei Iancu
*Director of the United States Patent and Trademark Office*